United States Patent
Pettersson et al.

(10) Patent No.: US 8,637,292 B2
(45) Date of Patent: Jan. 28, 2014

(54) POLYPEPTIDES HAVING FERULOYL ESTERASE ACTIVITY AND NUCLEIC ACIDS ENCODING THE SAME

(75) Inventors: Dan Pettersson, Lynge (DK); Wenping Wu, Beijing (CN); Lan Tang, Beijing (CN); Ye Liu, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 173 days.

(21) Appl. No.: 13/143,790

(22) PCT Filed: Jan. 15, 2010

(86) PCT No.: PCT/EP2010/050466
§ 371 (c)(1),
(2), (4) Date: Jul. 8, 2011

(87) PCT Pub. No.: WO2010/084086
PCT Pub. Date: Jul. 29, 2010

(65) Prior Publication Data
US 2011/0277044 A1    Nov. 10, 2011

Related U.S. Application Data

(60) Provisional application No. 61/146,509, filed on Jan. 22, 2009.

(30) Foreign Application Priority Data

Jan. 21, 2009    (EP) .................................... 09151012

(51) Int. Cl.
C12N 9/24    (2006.01)
C12N 9/42    (2006.01)
C12P 21/02   (2006.01)
A23K 1/14    (2006.01)
A23K 3/02    (2006.01)

(52) U.S. Cl.
USPC ........ 435/200; 424/93.2; 424/94.2; 536/23.2; 435/71.1; 426/53; 426/54

(58) Field of Classification Search
None
See application file for complete search history.

(56) References Cited

FOREIGN PATENT DOCUMENTS

| WO | WO 02/12472 | 2/2002 |
| WO | WO 2005040107 A2 * | 5/2005 |
| WO | WO 2009076122 A1 * | 6/2009 |

OTHER PUBLICATIONS

Guo et al. 2004. Protein tolerance to random amino acid change. PNAS. 101(25):9205-9210.*
Palmiter et al. 1982. Dramatic growth of mice that develop from eggs microinjected with metallothionein-growth hormone fusion genes. Nature. 300:611-615.*
Udatha et al. 2012. Common and distant structural characteristics of feruloyl esterase families from *Aspergillus oryzae*. PLoS One. 7(6):1-14.*
Uniprot. 2007. Attached document detailing Accession A2QVF5_ASPNC. 2 pages.*
Wong. 2006. Feruloyl esterase: A key enzyme in biomass degradation. Appl. Biochem. Biotech. 133:87-112.*
Benoit et al Biotechnol Lett vol. 30, No. 3, pp. 387-396 (2008).
Castanares et al, Enzyme Microb Technol, vol. 14, pp. 875-884 (1992).
Database Uniprot—Acces No. A2QAH7 (Jul. 17, 2009).
Database Uniprot—Acces No. A2QVF5 (2007).
Database Uniprot—Acces No. A6RKM1(2007).
Database UniProt—Acces No. B6QRY4 (2008).
Database UniProt—Acces No. Q4WDX0 (2005).
Database Uniprot—Acces No. Q2UH24 (2006).
Devries et al Appl Environ Microbiol, vol. 63, No. 12, pp. 4638-4644 (1997).
Faulds et al, J Gen Microbiol, vol. 137, pp. 2339-2345 (1991).
Faulds et al, Microbiol, vol. 140, pp. 779-787 (1994).
Kroon et al, Biotechnol Appl Biochem, vol. 23, pp. 255-262 (1996).
Panda et al, Appl Microbiol Biotechnol, vol. 67, No. 2, pp. 160-169 (2005).
Topakas et al Process Biochem, vol. 42, No. 4, pp. 497-509 (2007).

* cited by examiner

Primary Examiner — Anne Kubelik
Assistant Examiner — Jeffrey Bolland
(74) Attorney, Agent, or Firm — Kristin J. McNamara

(57) ABSTRACT

The present invention relates to isolated polypeptides having esterase activity and isolated polynucleotides encoding the polypeptides. The invention also relates to nucleic acid constructs, vectors, and host cells comprising the polynucleotides as well as methods of producing and using the polypeptides.

15 Claims, No Drawings

POLYPEPTIDES HAVING FERULOYL ESTERASE ACTIVITY AND NUCLEIC ACIDS ENCODING THE SAME

CROSS-REFERENCE TO RELATED APPLICATIONS

This application is a 35 U.S.C. 371 national application of PCT/EP2010/050466 filed Jan. 15, 2010, which claims priority or the benefit under 35 U.S.C. 119 of European application no. 09151012.3 filed Jan. 21, 2009 and U.S. provisional application No. 61/146,509 filed Jan. 22, 2009, the contents of which are fully incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference. For complete information see last page of the description.

FIELD OF THE INVENTION

The present invention relates to isolated polypeptides having esterase activity and isolated nucleic acid sequences encoding the polypeptides. The invention also relates to nucleic acid constructs, vectors, and host cells comprising the nucleic acid sequences as well as methods for producing and using the polypeptides.

BACKGROUND OF THE INVENTION

Plant cell wall polysaccharides constitute 90% of the plant cell wall and can be divided into three groups: cellulose, hemicellulose, and pectin. Cellulose represents the major constituent of cell wall polysaccharides. Hemicelluloses are the second most abundant constituent of plant cell walls. The major hemicellulose polymer is xylan. The biodegradation of the xylan backbone depends on two classes of enzymes: endoxylanases and beta-xylosidases. Endoxylanases (EC 3.2.1.8) cleave the xylan backbone into smaller oligosaccharides, which can be further degraded to xylose by beta-xylosidases (EC 3.2.1.37). Other enzymes involved in the degradation of xylan include, for example, acetylxylan esterase, arabinase, alpha-glucuronidase, esterase, and p-coumaric acid esterase.

WO02/12472 disclosed esterase which is capable of stereoselective hydrolysis of chiral esters and of hydrolyzing ferulic acid esters.

Faulds and Williamson, 1991, *J. Gen. Microbiol.* 137 2339-2345, describe the purification and characterization of 4-hydroxy-3-methoxy-cinnamic (ferulic) acid esterase from *Streptomyces olivochromogenes*. Faulds and Williamson, 1994, *Microbiology* 140 779-787, describe the purification and characterization of a feruloyl esterase from *Aspergillus niger*. Kroon et al., 1996, *Biotechnol. Appl. Biochem.* 23 255-262, describe the purification and characterisation of a novel esterase induced by growth of *Aspergillus niger* on sugarbeet pulp. deVries et al., 1997, *Appl. Environ. Microbiol.* 63 4638-4644, disclose the esterase genes from *Aspergillus niger* and *Aspergillus tubingensis*. Castanares et al., 1992, *Enzyme Microbiol. Technol.* 14 875-884, describe the purification and properties of a feruloyl/p-coumaroyl esterase from the fungus *Penicillium pinophilum*.

The present invention relates to polypeptides having esterase activity and polynucleotides encoding the polypeptides.

SUMMARY OF THE INVENTION

The inventors have isolated an esterase from *Myrothecium* sp. strain which has esterase activity. The novel esterase has a very low identity of less than 30% to known amino acid sequences. The inventors also isolated a gene encoding the novel esterase and cloned it into an *E. coli* strain.

The present invention relates to isolated polypeptides having esterase activity selected from the group consisting of:

(a) a polypeptide comprising an amino acid sequence having at least 45% identity to the mature polypeptide of SEQ ID NO: 2;

(b) a polypeptide encoded by a polynucleotide that hybridizes under at least medium stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii);

(c) a polypeptide encoded by a polynucleotide comprising a nucleotide sequence having at least 45% identity to the mature polypeptide coding sequence of SEQ ID NO: 1;

(d) a variant comprising a substitution, deletion, and/or insertion of one or several amino acids of the mature polypeptide of SEQ ID NO: 2.

The present invention also relates to isolated polynucleotides encoding polypeptides having esterase activity, selected from the group consisting of:

(a) a polynucleotide encoding a polypeptide comprising an amino acid sequence having at least 45% identity to the mature polypeptide of SEQ ID NO: 2;

(b) a polynucleotide that hybridizes under at least medium stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii);

(c) a polynucleotide comprising a nucleotide sequence having at least 45% identity to the mature polypeptide coding sequence of SEQ ID NO: 1;

(d) a polynucleotide encoding a variant comprising a substitution, deletion, and/or insertion of one or several amino acids of the mature polypeptide of SEQ ID NO: 2.

The present invention also relates to nucleic acid constructs, recombinant expression vectors, recombinant host cells comprising the polynucleotides, and methods of producing a polypeptide having esterase activity.

The present invention also relates to methods of inhibiting the expression of a polypeptide in a cell, comprising administering to the cell or expressing in the cell a double-stranded RNA (dsRNA) molecule, wherein the dsRNA comprises a subsequence of a polynucleotide of the present invention. The present also relates to such a double-stranded inhibitory RNA (dsRNA) molecule, wherein optionally the dsRNA is a siRNA or an miRNA molecule.

The present invention also relates to methods for degrading a material comprising a xylan.

The present invention also relates to plants comprising an isolated polynucleotide encoding such a polypeptide having esterase activity.

The present invention also relates to methods of producing such a polypeptide having esterase, comprising: (a) cultivating a transgenic plant or a plant cell comprising a polynucleotide encoding such a polypeptide having esterase activity under conditions conducive for production of the polypeptide; and (b) recovering the polypeptide.

The present invention further relates to nucleic acid constructs comprising a gene encoding a protein, wherein the gene is operably linked to a nucleotide sequence encoding a signal peptide comprising or consisting of amino acids 1 to 20 of SEQ ID NO: 2, wherein the gene is foreign to the nucleotide sequence.

BRIEF DESCRIPTION OF DRAWINGS

Esterase Activity:

The term "esterase activity" is defined as hydrolase activity (EC 3.1.1.) that splits esters into an acid and an alcohol in a chemical reaction with water called hydrolysis. For purposes of the present invention, esterase activity is determined according to the procedure of determination of esterase activity in pNPB substrate described in the Example 1.

It is well-known in the art that esterase under (EC 3.1.1.1) can be chosen from, for example, Feruloyl esterase (EC 3.1.1.73), Acetylxylan esterase (EC 3.1.1.72), Protein-glutamate methylesterase (EC 3.1.1.61), Carboxylesterase (EC 3.1.1.1), Arylesterase (EC 3.1.1.2), Acetylesterase (EC 3.1.1.6), Cholinesterase (EC 3.1.1.8), Sterol esterase (EC 3.1.1.13), Alpha-amino-acid esterase (EC 3.1.1.43) and so on.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the esterase activity of the mature polypeptide of SEQ ID NO: 2.

Isolated Polypeptide:

The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially Pure Polypeptide:

The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature Polypeptide:

The term "mature polypeptide" is defined herein as a polypeptide having esterase activity that is in its final form following translation and any post-translational modifications, such as N-terminal processing, C-terminal truncation, glycosylation, phosphorylation, etc. In a preferred aspect, the mature polypeptide is amino acids 21 to 520 of SEQ ID NO: 2 based on the SignalP program that predicts amino acids 1 to 20 of SEQ ID NO: 2 are a signal peptide.

Mature Polypeptide Coding Sequence:

The term "mature polypeptide coding sequence" is defined herein as a nucleotide sequence that encodes a mature polypeptide having esterase activity. In a preferred aspect, the mature polypeptide coding sequence is nucleotides 61 to 1560 of SEQ ID NO: 1 based on the SignalP program that predicts nucleotides 1 to 60 of SEQ ID NO: 1 encode a signal peptide.

Identity:

The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

$$(\text{Identical Deoxyribonucleotides} \times 100)/(\text{Length of Alignment} - \text{Total Number of Gaps in Alignment})$$

Homologous Sequence:

The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Myrothecium* sp. esterase of SEQ ID NO:2 or the mature polypeptide thereof.

Polypeptide Fragment:

The term "polypeptide fragment" is defined herein as a polypeptide having one or more (several) amino acids deleted from the amino and/or carboxyl terminus of the mature polypeptide of SEQ ID NO: 2; or a homologous sequence thereof; wherein the fragment has esterase activity. In a preferred aspect, a fragment contains at least 250 amino acid residues, more preferably at least 300 amino acid residues, and most preferably at least 450 amino acid residues, of the mature polypeptide of SEQ ID NO: 2 or a homologous sequence thereof.

Subsequence:

The term "subsequence" is defined herein as a nucleotide sequence having one or more (several) nucleotides deleted from the 5' and/or 3' end of the mature polypeptide coding sequence of SEQ ID NO: 1; or a homologous sequence thereof; wherein the subsequence encodes a polypeptide fragment having esterase activity. In a preferred aspect, a subsequence contains at least 750 nucleotides, more preferably at least 900 nucleotides, and most preferably at least 1350 nucleotides of the mature polypeptide coding sequence of SEQ ID NO: 1 or a homologous sequence thereof.

Allelic Variant:

The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated Polynucleotide:

The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially Pure Polynucleotide:

The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding Sequence:

When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic or recombinant nucleotide sequence.

cDNA:

The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic Acid Construct:

The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control Sequences:

The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably Linked:

The term "operably linked" denotes herein a configuration in which a control sequence is placed at an appropriate position relative to the coding sequence of the polynucleotide sequence such that the control sequence directs the expression of the coding sequence of a polypeptide.

Expression:

The term "expression" includes any step involved in the production of the polypeptide including, but not limited to, transcription, post-transcriptional modification, translation, post-translational modification, and secretion.

Expression Vector:

The term "expression vector" is defined herein as a linear or circular DNA molecule that comprises a polynucleotide encoding a polypeptide of the present invention and is operably linked to additional nucleotides that provide for its expression.

Host Cell:

The term "host cell", as used herein, includes any cell type that is susceptible to transformation, transfection, transduction, and the like with a nucleic acid construct or expression vector comprising a polynucleotide of the present invention.

Modification:

The term "modification" means herein any chemical modification of the polypeptide consisting of the mature polypeptide of SEQ ID NO:2; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial Variant:

When used herein, the term "artificial variant" means a polypeptide having esterase activity produced by an organism expressing a modified polynucleotide sequence of the mature polypeptide coding sequence of SEQ ID NO:1; or a homologous sequence thereof. The modified nucleotide sequence is obtained through human intervention by modification of the polynucleotide sequence disclosed in SEQ ID NO:1; or a homologous sequence thereof.

DETAILED DESCRIPTION OF THE INVENTION

Polypeptides Having Esterase Activity

In a first aspect, the present invention relates to isolated polypeptides comprising an amino acid sequence having a degree of identity to the mature polypeptide of SEQ ID NO:2 of preferably at least 45%, more preferably at least 50%, more preferably at least 55%, more preferably at least 65%, more preferably at least 70%, more preferably at least 75%, even more preferably at least 80%, most preferably at least 85%, and even most preferably at least 90%, at least 95%, at least 96%, at least 97%, at least 98%, or at least 99%, which have esterase activity (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO:2.

A polypeptide of the present invention preferably comprises the amino acid sequence of SEQ ID NO:2 or an allelic variant thereof; or a fragment thereof having esterase activity. In a preferred aspect, the polypeptide comprises the amino acid sequence of SEQ ID NO:2. In another preferred aspect, the polypeptide comprises the mature polypeptide of SEQ ID NO:2. In another preferred aspect, the polypeptide comprises amino acids 21 to 520 of SEQ ID NO:2, or an allelic variant thereof; or a fragment thereof having esterase activity. In another preferred aspect, the polypeptide comprises amino acids 21 to 520 of SEQ ID NO:2. In another preferred aspect, the polypeptide consists of the amino acid sequence of SEQ ID NO:2 or an allelic variant thereof; or a fragment thereof having esterase activity. In another preferred aspect, the polypeptide consists of the amino acid sequence of SEQ ID NO:2. In another preferred aspect, the polypeptide consists of the mature polypeptide of SEQ ID NO:2. In another preferred aspect, the polypeptide consists of amino acids 21 to 520 of SEQ ID NO:2 or an allelic variant thereof; or a fragment thereof having esterase activity. In another preferred aspect, the polypeptide consists of amino acids 21 to 520 of SEQ ID NO:2.

In a second aspect, the present invention relates to isolated polypeptides having esterase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO:1, (ii) the cDNA sequence contained in the mature polypeptide coding sequence of SEQ ID NO:1, (iii) a subsequence of (i) or (ii), or (iv) a full-length complementary strand of (i), (ii), or (iii) (J. Sambrook, E. F. Fritsch, and T. Maniatis, 1989, Molecular Cloning, A Laboratory Manual, 2d edition, Cold Spring Harbor, N.Y.). A subsequence of the mature polypeptide coding sequence of SEQ ID NO:1 contains at least 100 contiguous nucleotides or preferably at least 200 contiguous nucleotides. Moreover, the subsequence may encode a polypeptide fragment having esterase activity. In a preferred aspect, the complementary strand is the full-length complementary strand of the mature polypeptide coding sequence of SEQ ID NO:1.

The nucleotide sequence of SEQ ID NO:1; or a subsequence thereof; as well as the amino acid sequence of SEQ ID NO:2; or a fragment thereof; may be used to design nucleic acid probes to identify and clone DNA encoding polypeptides having esterase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having esterase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO:1; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO:1; cDNA sequence contained in the mature polypeptide coding sequence of SEQ ID NO:1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO:1. In another preferred aspect, the nucleic acid probe is nucleotides 61 to 1560 of SEQ ID NO:1. In another preferred aspect, the nucleic acid probe is a polynucleotide sequence that encodes the polypeptide of SEQ ID NO:2, or a subsequence thereof. In another preferred aspect, the nucleic acid probe is SEQ ID NO:1. In another preferred aspect, the nucleic acid probe is the polynucleotide sequence contained in plasmid which is contained in E. coli DSM19428, wherein the polynucleotide sequence thereof encodes a polypeptide having esterase activity. In another preferred aspect, the nucleic acid probe is the mature polypeptide coding region contained in plasmid which is contained in *E. coli* DSM19428.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having esterase activity encoded by polynucleotides comprising or consisting of nucleotide sequences that have a degree of identity to the mature polypeptide coding sequence of SEQ ID NO: 1 of preferably at least 45%, more preferably at least 50%, more preferably at least 55%, more preferably at least 65%, more preferably at least 75%, more preferably at least 80%, more preferably at least 85%, even more preferably at least 90%, most preferably at least 95%, and even most preferably 96%, 97%, 98%, or 99%, which encode an active polypeptide. See polynucleotide section herein.

In a fourth aspect, the present invention relates to artificial variants comprising a substitution, deletion, and/or insertion of one or more (or several) amino acids of the mature polypeptide of SEQ ID NO:2; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e. esterase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO95/22625. Other methods that can be used include error-prone PCR, phage display (e.g., Lowman et al., 1991, *Biochem.* 30: 10832-10837; U.S. Pat. No. 5,223,409; WO92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO:2, such as amino acids 21 to 520 of SEQ ID NO:2, is 10, preferably 9, more preferably 8, more preferably 7, more preferably at most 6, more preferably 5, more preferably 4, even more preferably 3, most preferably 2, and even most preferably 1.

Sources of Polypeptides Having Esterase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having esterase activity of the present invention may be a bacterial poly-peptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having esterase activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having esterase activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having esterase activity.

In another preferred aspect, the polypeptide is a *Streptococcus equisimilis, Streptococcus pyogenes, Streptococcus uberis,* or *Streptococcus equi* subsp. *Zooepidemicus* polypeptide having esterase activity.

In another preferred aspect, the polypeptide is a *Streptomyces achromogenes, Streptomyces avermitilis, Streptomyces coelicolor, Streptomyces griseus,* or *Streptomyces lividans* polypeptide having esterase activity.

A polypeptide having esterase activity of the present invention may also be a fungal polypeptide, and more preferably a yeast polypeptide such as a *Candida, Kluyveromyces, Pichia, Saccharomyces, Schizosaccharomyces,* or *Yarrowia* polypeptide having esterase activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having esterase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having esterase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* polypeptide having esterase activity.

In another preferred aspect, the polypeptide is a *Myrothecium* polypeptide. In a more preferred aspect, the polypeptide is a *Myrothecium* sp. polypeptide having esterase activity, e.g., the polypeptide comprising the mature polypeptide of SEQ ID NO:2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention.

Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having esterase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, Drug Discovery World 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having esterase activity of the present invention.

In a preferred aspect, the nucleotide sequence comprises or consists of SEQ ID NO:1. In another more preferred aspect, the nucleotide sequence comprises or consists of the sequence contained in plasmid which is contained in *E. coli* DSM19428. In another preferred aspect, the nucleotide sequence comprises or consists of the mature polypeptide coding sequence of SEQ ID NO:1. In another preferred aspect, the nucleotide sequence comprises or consists of nucleotides 61 to 1560 of SEQ ID NO:1. In another more preferred aspect, the nucleotide sequence comprises or consists of the mature polypeptide coding sequence contained in plasmid which is contained in *E. coli* DSM19428. The present invention also encompasses nucleotide sequences that encode polypeptides comprising or consisting of the amino acid sequence of SEQ ID NO:2 or the mature polypeptide thereof, which differ from SEQ ID NO:1 or the mature polypeptide coding sequence thereof by virtue of the degeneracy of the genetic code. The present invention also relates to subsequences of SEQ ID NO:1 that encode fragments of SEQ ID NO:2 that have esterase activity.

The present invention also relates to mutant polynucleotides comprising or consisting of at least one mutation in the mature polypeptide coding sequence of SEQ ID NO:1, in which the mutant nucleotide sequence encodes the mature polypeptide of SEQ ID NO:2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Myrothecium*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO:1 of preferably at least 45%, more preferably at least 50%, more preferably at least 65%, more preferably at least 75%, more preferably at least 80%, more preferably at least 85%, even more preferably at least 90%, most preferably at least 95%, and even most preferably at least 96%, at least 97%, at least 98%, or at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO:1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution see e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for esterase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO:1, (ii) the cDNA sequence contained in the mature polypeptide coding sequence of SEQ ID NO:1, or (iii) a full-length complementary strand of (i) or (ii); or allelic variants and subsequences thereof (Sambrook et al., 1989, supra), as defined herein. In a preferred aspect, the complementary strand is the full-length complementary strand of the mature polypeptide coding sequence of SEQ ID NO:1.

The present invention also relates to isolated polynucleotides obtained by (a) hybridizing a population of DNA under very low, low, medium, medium-high, high, or very high stringency conditions with (i) the mature polypeptide coding sequence of SEQ ID NO:1, (ii) the cDNA sequence contained in the mature polypeptide coding sequence of SEQ ID NO:1, or (iii) a full-length complementary strand of (i) or (ii); and (b) isolating the hybridizing polynucleotide, which encodes a polypeptide having esterase activity. In a preferred aspect, the complementary strand is the full-length complementary strand of the mature polypeptide coding sequence of SEQ ID NO:1.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO00/56900), *Fusarium venenatum* Daria (WO00/56900), *Fusarium venenatum* Quinn (WO00/56900), *Fusarium oxysporum* trypsin-like protease (WO96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), *Bacillus clausii* alcaline protease (aprH) and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 20 of SEQ ID NO:2. In another preferred aspect, the signal peptide coding sequence comprises or consists of nucleotides 1 to 60 of SEQ ID NO:1.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, xyl and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus*, *Streptococcus*, *Streptomyces*, *Staphylococcus*, *Enterococcus*, *Lactobacillus*, *Lactococcus*, *Clostridium*, *Geobacillus*, and *Oceanobacillus*. Gram negative bacteria include, but not limited to, *E. coli*, *Pseudomonas*, *Salmonella*, *Campylobacter*, *Helicobacter*, *Flavobacterium*, *Fusobacterium*, *Ilyobacter*, *Neisseria*, and *Ureaplasma*.

The bacterial host cell may be any *Bacillus* cell. *Bacillus* cells useful in the practice of the present invention include, but are not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

In a preferred aspect, the bacterial host cell is a *Bacillus amyloliquefaciens*, *Bacillus lentus*, *Bacillus licheniformis*, *Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis*, *Streptococcus pyogenes*, *Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes*, *Streptomyces avermitilis*, *Streptomyces coelicolor*, *Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP238023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a host cell under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO:1, wherein the mutant nucleotide sequence encodes a polypeptide that comprises or consists of the mature polypeptide of SEQ ID NO:2, and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of a esterase product, or disappearance of a esterase substrate. For example, a esterase assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having esterase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, triticale (stabilized hybrid of wheat (Triticum) and rye (Secale), and maize (corn).

Examples of dicot plants are tobacco, legumes, such as sunflower (Helianthus), cotton (Gossypium), lupins, potato, sugar beet, pea, bean and soybean, and cruciferous plants (family Brassicaceae), such as cauliflower, rape seed, and the closely related model organism *Arabidopsis thaliana*. Low-phytate plants as described e.g. in U.S. Pat. No. 5,689,054 and U.S. Pat. No. 6,111,168 are examples of engineered plants.

Examples of plant parts are stem, callus, leaves, root, fruits, seeds, and tubers, as well as the individual tissues comprising these parts, e.g. epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g. embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific cell compartment, tissue or plant part such as seeds or leaves. Regulatory sequences are, for example, described by Tague et al., 1988, Plant Physiology 86: 506.

For constitutive expression, the following promoters may be used: The 35S-CaMV promoter (Franck et al., 1980, Cell 21: 285-294), the maize ubiquitin 1 (Christensen A H, Sharrock R A and Quail 1992. Maize polyubiquitin genes: structure, thermal perturbation of expression and transcript splicing, and promoter activity following transfer to protoplasts by electroporation), or the rice actin 1 promoter (Plant Mo. Biol.

18, 675-689.; Zhang W, McElroy D. and Wu R 1991, Analysis of rice Act1 5' region activity in transgenic rice plants. Plant Cell 3, 1155-1165). Organ-specific promoters may be, for example, a promoter from storage sink tissues such as seeds, potato tubers, and fruits (Edwards & Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant and Cell Physiology 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiology 102: 991-1000, the *chlorella* virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588). Likewise, the promoter may be inducible by abiotic treatments such as temperature, drought or alterations in salinity or inducible by exogenously applied substances that activate the promoter, e.g. ethanol, oestrogens, plant hormones like ethylene, abscisic acid, gibberellic acid, and/or heavy metals.

A promoter enhancer element may also be used to achieve higher expression of the ENZYME in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium tumefaciens*-mediated gene transfer is the method of choice for generating transgenic dicots (for a review, see Hooykas and Schilperoort, 1992, Plant Molecular Biology 19: 15-38), and it can also be used for transforming monocots, although other transformation methods are more often used for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, Plant Journal 2: 275-281; Shimamoto, 1994, Current Opinion Biotechnology 5: 158-162; Vasil et al., 1992, Bio/Technology 10: 667-674). An alternative method for transformation of monocots is based on protoplast transformation as described by Omirulleh et al., 1993, Plant Molecular Biology 21: 415-428.

Following transformation, the transformants having incorporated therein the expression construct are selected and regenerated into whole plants according to methods well-known in the art. Often the transformation procedure is designed for the selective elimination of selection genes either during regeneration or in the following generations by using e.g. co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a nucleic acid sequence encoding a polypeptide having ENZYME activity of the present invention under conditions conducive for production of the polypeptide; and (b) recovering the polypeptide.

Compositions

In a still further aspect, the present invention relates to compositions comprising a polypeptide of the present invention.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptides or polypeptide compositions of the invention.

Animal Feed

The present invention is also directed to methods for using the polypeptides having esterase activity in animal feed, as well as to feed compositions and feed additives comprising the polypeptides of the invention.

The term animal includes all animals, including human beings. Examples of animals are non-ruminants, and ruminants. Ruminant animals include, for example, animals such as sheep, goat, and cattle, e.g. cow such as beef cattle and dairy cows. In a particular embodiment, the animal is a non-ruminant animal. Non-ruminant animals include mono-gastric animals, e.g. pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

The term feed or feed composition means any compound, preparation, mixture, or composition suitable for, or intended for intake by an animal.

In the use according to the invention the esterase can be fed to the animal before, after, or simultaneously with the diet. The latter is preferred.

In a particular embodiment, the esterase, in the form in which it is added to the feed, or when being included in a feed additive, is well-defined. Well-defined means that the esterase preparation is at least 50% pure as determined by Size-exclusion chromatography (see Example 12 of WO01/58275). In other particular embodiments the esterase preparation is at least 60, 70, 80, 85, 88, 90, 92, 94, or at least 95% pure as determined by this method.

A well-defined esterase preparation is advantageous. For instance, it is much easier to dose correctly to the feed an esterase that is essentially free from interfering or contaminating other esterases. The term dose correctly refers in particular to the objective of obtaining consistent and constant results, and the capability of optimising dosage based upon the desired effect.

For the use in animal feed, however, the esterase need not be that pure; it may e.g. include other enzymes, in which case it could be termed a esterase preparation.

The esterase preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original esterase preparation, whether used according to (a) or (b) above.

Esterase preparations with purities of this order of magnitude are in particular obtainable using recombinant methods of production, whereas they are not so easily obtained and also subject to a much higher batch-to-batch variation when the esterase is produced by traditional fermentation methods.

Such esterase preparation may of course be mixed with other enzymes.

The esterase can be added to the feed in any form, be it as a relatively pure esterase, or in admixture with other components intended for addition to animal feed, i.e. in the form of animal feed additives, such as the so-called pre-mixes for animal feed.

In a further aspect the present invention relates to compositions for use in animal feed, such as animal feed, and animal feed additives, e.g. premixes.

Apart from the esterase of the invention, the animal feed additives of the invention contain at least one fat-soluble vitamin, and/or at least one water soluble vitamin, and/or at least one trace mineral, and/or at least one macro mineral.

Further, optional, feed-additive ingredients are colouring agents, e.g. carotenoids such as beta-carotene, astaxanthin, and lutein; aroma compounds; stabilisers; antimicrobial peptides; polyunsaturated fatty acids; reactive oxygen generating species; and/or at least one other enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4.); phospholipase A1 (EC 3.1.1.32); phospholipase A2 (EC 3.1.1.4); lysophospholipase (EC 3.1.1.5); phospholipase C (EC 3.1.4.3); phospholipase D (EC 3.1.4.4); amylase such as, for example, alpha-amylase (EC 3.2.1.1); beta-glucanase (EC 3.2.1.4 or EC 3.2.1.6) and/or arabinofuranosidase (EC 3.2.1.55).

In a particular embodiment these other enzymes are well-defined (as defined above for esterase preparations).

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO03/044049 and WO03/048148, as well as variants or fragments of the above that retain antimicrobial activity.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a synthethase.

Usually fat- and water-soluble vitamins, as well as trace minerals form part of a so-called premix intended for addition to the feed, whereas macro minerals are usually separately added to the feed. Either of these composition types, when enriched with an esterase of the invention, is an animal feed additive of the invention.

In a particular embodiment, the animal feed additive of the invention is intended for being included (or prescribed as having to be included) in animal diets or feed at levels of 0.005 to 10%, particularly 0.01 to 5%, more particularly 0.02 to 2% and even more particularly 0.2 to 1% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO01/58275. Nutritional requirement means that these components should be provided in the diet in the concentrations indicated.

In the alternative, the animal feed additive of the invention comprises at least one of the individual components specified in Table A of WO01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO01/58275, columns 2-3. Fish diets can be characterised as indicated in column 4 of this Table B. Furthermore such fish diets usually have a crude fat content of 200-310 g/kg.

WO01/58275 corresponds to U.S. Pat. No. 6,960,462 which is hereby incorporated by reference.

An animal feed composition according to the invention has a crude protein content of 50-800 g/kg, and furthermore comprises at least one esterase as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & Iooijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix.

The final enzyme concentration in the diet is within the range of 0.01-200 mg enzyme protein per kg diet, for example in the range of 0.2-30 mg, preferably 0.5 to 1.5 mg enzyme protein per kg animal diet. For the enzyme composition comprising xylanase and esterase, the final enzyme concentration will be typically 0.5 to 1 mg per kg animal diet.

The esterase should of course be applied in an effective amount, i.e. in an amount adequate for improving solubilisation and/or improving nutritional value of feed. It is at present contemplated that the enzyme is administered in one or more of the following amounts (dosage ranges): 0.01-200; 0.01-100; 0.5-100; 1-50; 5-100; 10-100; 0.05-50; or 0.10-10—all these ranges being in mg esterase protein per kg feed (ppm).

For determining mg esterase protein per kg feed, the esterase is purified from the feed composition, and the specific activity of the purified esterase is determined using a relevant assay (see under determination of esterase). The esterase activity of the feed composition as such is also determined using the same assay, and on the basis of these two determinations, the dosage in mg esterase protein per kg feed is calculated.

The same principles apply for determining mg esterase protein in feed additives. Of course, if a sample is available of the esterase used for preparing the feed additive or the feed, the specific activity is determined from this sample (no need to purify the esterase from the feed composition or the additive).

EXAMPLES

Reagents, Media, and Equipment

Reagents:
Unless otherwise specified, the chemicals used were commercial products of at least reagent grade.
pNP-Substrates:
pNPB: p-Nitrophenyl Butyrate (Sigma N9876),
pNPA: p-Nitrophenyl Acetate (Sigma N8130),
pNPP: p-Nitrophenyl palmitate (Sigma N2752),
pNNAG: p-Nitrophenyl N-Acetyl-β-D-Glucosaminide (Sigma N9376).
EDTA (Gibco BRL Cat. No. 15576-028)
IPTG (Promega, Cat. No. V3951)
X-gal (Promega, Cat. No. V3941)
Ampicillin Sodium Salt (GIBCOL Cat. No. 11593-019)
LMP agarose (Promega, Cat. No. V2111)
BETEB: Terephthalic acid bis(2-hydroxyethyl)ester dibenzoate is herein abbreviated as BETEB (benzoyl-ethylene-terephthalic-ethelene-benzoate). It was prepared from terephthalic acid bis(2-hydroxyethyl) ester and benzoic acid.
Media:
LB liquid medium: To 950 ml of deionized $H_2O$, add: 10 g bacto-tryptone, 5 g bacto-yeast extract, 10 g NaCl. Shake until the solutes have dissolved. Adjust the pH to 7.0 with 5 N NaOH (~0.2 ml). Adjust the volume of the solution to 1 liter with deionized $H_2O$. Sterilize by autoclaving for 20 minutes at 15 lb/sq. in. on liquid cycle.
LB plates with ampicillin/IPTG/X-Gal: Add 15 g agar to 1 liter of LB medium. Add ampicillin to a final concentration of 100 μg/ml, then supplement with 0.5 mM IPTG and 80 μg/ml X-gal and pour the plates.
SOC liquid medium: 2% Tryptone, 0.5% Yeast Extract, 10 mM NaCl, 2.5 mM KCl, 10 mM $MgCl_2$, 10 mM $MgSO_4$, 20 mM glucose
TAE buffer: 0.04 M Tris-acetate, 0.001M EDTA
1% LMP agarose gel: Add 1 g LMP agarose into 100 ml 1×TAE buffer.
YS medium: To 1 liter water add: 10 g peptone, 10 g yeast extract, 5 g glucose, 5 g $K_2HPO_4$, 1 g $MgSO_4.7H_2O$, 20 ml olive oil.
MD medium: 1.34% YNB, $4\times10^{-5}$% biotin, 2% dextrose
BMGY (Buffered Glycerol-complex Medium): 1% yeast extract, 2% peptone, 100 mM potassium phosphate (pH6.0), 1.34% YNB, $4\times10^{-5}$% biotin, 1% glycerol
BMMY (Buffered Methanol-complex Medium) 1% yeast extract, 2% peptone, 100 mM potassium phosphate (pH 6.0), 1.34% YNB, $4\times10-5$% biotin, 0.5% methanol.
Equipment, Including Various Kits:
5 K membrane (Millipore BIOMAX-5, 13442AM)
0.45 μm filter (Nalgene 190-2545)
0.45 μm polycarbonate filters (Sartorius)
Q Sepharose FF column (Amersham Pharmacia 17-0510-01)
Superdex75 column (Amersham Pharmacia 17-1047-01)
Superdex Peptide PE (7.5×300 mm) gelfiltration column (Global)
IEF-gel (Amersham Pharmacia 80-1124-80)
Thermomixer comfort (Eppendorf)
Spectrophotometer DU7500 (Beckman)
GeneAmp PCR System 9700(PE)
Vac-Man Jr. Laboratory Vacuum Manifold (Promega, Cat. No. A7660)
BioRad GenePulser II
RNeasy Plant Mini Kit (50) (QIAGEN, Cat. No. 74904)
DNeasy Plant Mini Kit (50) (QIAGEN, Cat. No. 69104)
3' RACE Kit (GIBCO, Cat. No. 18373-019) including Adapter primer, and AUAP
dNTP mix (100 mM, Promega, Cat. No. U1330)
TaqDNA polymerase system (Promega, Cat. No. M1661) including PCR buffer (200 mM Tris-HCl (pH 8.4), 500 mM KCl)
PCR Preps DNA Purification System (Promega, Cat. No. A7170)
pGEM-T Vector System (Promega, Cat. No. A3600) including T4 DNA Ligase 2× Buffer
JM109 high efficiency competent cells (Promega, Cat. No. L1001)
ElectroMax™ DH10B competent cell (Invitrogen, Cat. No. 18290-015)
Minipreps DNA Purification System (Promega, Cat. No. A7100)
BigDye Terminator Cycle Sequencing Ready Reaction Kit (PE Applied Biosystems, Cat. No. 4303149)
DNA Walking™ SpeedUp Kit (SeeGene, Cat. No. #K1502)
ABI Prism 377 DNA sequencer (PE)
pfu DNA polymerase system (Promega, Cat. No. M7741)

SnaB I (Promega R6791)
Not I (Promega R6431)
Bgl II (Promega R6071)

Example 1

Esterase Assays

Agarose Plate Assay:
Agarose plates containing 1% agarose in phosphate-citrate buffer pH 8.5, 0.1% BETEB; 20 µl sample was applied into d=4 mm holes in the agarose plates with BETEB substrate, incubation at 45° C. for 12-16 hours. Enzyme activity was identified by clean halos.

BETEB Eppendorf Tube Assay
A solution of 0.08% of the BETEB substrate is suspended in Tri-HCl buffer pH 8.5 while stirring (For the pH profile part of Example 4, the buffer system pH 3 to pH 11 was used instead). The solution is distributed while stirring to Eppendorf tube (100 µl to each well), 30 µl enzyme sample is added and the plates are incubated in an Eppendorf Thermomixer for 30 minutes at 50° C. and 1200 rpm. Denatured enzyme sample (100° C. boiling for 20 min) is used as a blank. After incubation the reaction is stopped by transferring the tube onto ice and then centrifuged for 10 minutes at 10000 rpm and 4° C. 60 µl of supernatant is transferred to a microtiter plate and the absorbance at 230 nm is measured using a BioRad Microplate Reader.

Isoelectric Focusing:
Isoelectric focusing was carried out in precast Ampholine PAG plates pH 3.5-9.5 (Pharmacia, Sweden) according to the manufacturer's instructions. The samples were applied in triplicate and after electrophoresis the gel was divided into three. An overlay containing 1% agarose and 0.1% BETEB in buffer pH 8.5 was poured onto each part of gel. Incubation at 45° C. for 12-16 hours. Enzyme activity and pI of enzyme protein was identified by clean zones.

Determination of Esterase Activity in pNPB Substrate
Esterase activity is determined using p-Nitrophenyl Butyrate as substrate. The enzyme preparation is diluted to provide less than 15% conversion of p-Nitrophenyl Butyrate by making an initial dilution in a 1.5 ml microcentrifuge tube with 50 mM sodium acetate pH 5.0 followed by 2-fold serial dilutions with 50 mM sodium acetate pH 5.0. Then 100 µl aliquots of the diluted enzyme are transferred to wells of a 96-well plate.

A p-Nitrophenyl Butyrate stock solution is made by dissolving p-Nitrophenyl Butyrate in dimethylsulfoxide (DMSO) to constitute a 0.1 M solution. Before assay, a sample of the stock solution is diluted 100-fold in 50 mM sodium acetate pH 5.0 to make a 1 mM solution. A 100 µl volume of 1 mM p-Nitrophenyl Butyrate is mixed with each dilution of the enzyme and then incubated at 25° C. for 10 minutes. Substrate alone, enzyme alone, and buffer alone are run as controls. p-Nitrophenol standard solutions of 0.25, 0.2, 0.1, 0.05, and 0.02 mM are prepared by diluting a 10 mM stock solution in 50 mM sodium acetate pH 5.0. At 10 minutes, 50 µl of 1.0 M Tris-HCl pH 8.0 buffer is added to each well (including samples, substrate control, enzyme control, reagent control, and standards), mixed, and the absorbance at 405 nm immediately measured on a microtiter plate reader (BioRad). One unit of esterase activity is defined as the amount of enzyme capable of releasing 1 µmole of p-nitrophenolate anion per minute at pH 5, 25° C.

Example 2

Cultivation of Myrothecium sp. Strain

For inoculation, the fungal species Myrothecium sp. strain was grown on YS agar plate (Peptone 10 g/L, Yeast extract 10 g/L, Glucose 5 g/L, $K_2HPO_4$ 5 g/L, $MgSO_4.7H_2O$ 1 g/L, agar 20 g/L, pH 6.5) at 25° C. for 7 days and then stored in 4° C. before used for inoculation of shake flask. For crude enzyme production, the strains was inoculated in 500 ml shake flask with 50 ml YS media (Peptone 10 g/L, Yeast extract 10 g/L, Glucose 5 g/L, $K_2HPO_4$ 5 g/L, $MgSO_4.7H_2O$ 1 g/L, Olive oil, pH 6.5) and incubated under 160 rpm and 25° C. for 7 days. The culture broth was harvested by centrifugation (4000 rpm for 20 minutes at 4° C.).

Example 3

Purification of the Esterase from Myrothecium sp. Strain 1200 ml supernatant from Example 2 was precipitated with ammonium sulfate (80% saturation) and re-dissolved in 40 ml 25 mM Tris-HCl, pH 7.4 buffer. The resulting solution was dialyzed against 25 mM Tris-HCl buffer (pH 8.0) to remove salts. The final volume was 50 ml. The concentrated enzyme solution was loaded on to a Mono Q anion exchange column equilibrated with 25 mM Tris-HCl buffer, pH 8.0, and then the proteins were eluted with a linear gradient of 0-1 M NaCl. The effluent from the column was checked for absorption at 280 nm and fractions were assayed for enzyme activity by BETEB plate assay at pH 8.5. The active fractions were pooled and concentrated, and then apply the above concentrated fraction on to a Superdex 75 gel filtration column which had been previously equilibrated with 25 mM Tris-HCl buffer, pH 8.0, and elute the proteins with the same buffer. After enzyme assay the active fractions were pooled, concentrated again and dialyzed against 20 mM sodium acetate buffer, pH 5.0. The dialyzed samples were applied to a third column, Mono Q equilibrated with 20 mM sodium acetate buffer, pH 5.0. The proteins were eluted with a linear gradient of 0-1 M NaCl. Finally, the active fractions were pooled and used for characterization.

After the above purification procedures, samples were collected and checked for both activity (Agarose plate assay and overlay technique with BETEB) and also purity (SDS PAGE and IEF gel), then used for characterization.

On SDS-Page, 4 protein bands around the molecular weight 60 KDa were seen and supposed to be the corresponding enzyme protein. These protein bands were electro-blotted and the N-terminal sequences were determined. It was found that these 4 protein bands have the same N-terminal sequences: SCSPEVFSSVGIPKGEVL.

Overlay of BETEB substrate after running IEF gel showed that there was a single active fraction with pI around pH 3.5. The same N-terminal sequence and the same pI led the conclusion that they are the same protein.

Example 4

Characterization of the Esterase of Myrothecium sp. Strain

Temperature Profile
The relationship between temperature and enzyme activity was evaluated using both p-NPB and BETEB assay.

The enzyme is active in a wide range of temperatures from 20-70° C. and appears to have its optimum temperature around 50-60° C.

pH Profile
The relationship between pH and enzyme activity was evaluated using the both p-NPB and BETEB assay of Example 1 with the buffer system pH 3 to pH 11.

The enzyme appears to have activity in a broad pH-range from pH 4-10. The optimum pH is around 8-9.

Temperature Stability

For temperature stability measurements, the enzyme was incubated at 60 degree for different times (0, 1, 3, 4, 6, 7, 14, 24 hours), then the enzyme activity was assayed by using pNPB as substrate at pH 8.5.

The enzyme appears to be stable. It still has around 30% residue activity even after incubation 7 hours at 60 degree.

pNP Substrate Specificity

The substrate specificity of the enzyme was evaluated using different substrates including a few pNP-substrates (p-Nitrophenyl Butyrate (Sigma N9876), p-Nitrophenyl Acetate (Sigma N8130), p-Nitrophenyl palmitate (Sigma N2752), p-Nitrophenyl N-Acetyl-β-D-Glucosaminide (Sigma N9376), tannin, BETEB. The result was shown the following Table 1.

TABLE 1

Comparison of substrate specificity of the enzyme of the present invention

| Substrate | Enzyme of the present invention |
|---|---|
| Tannin | − |
| BETEB | + |
| pNPP | − |
| pNPB | + |
| pNPA | − |
| pNNAG | + |

From the above table, we can know the enzymes of the present invention have esterase activity. It is active on pNPB substrate and BETEB substrate.

N-Terminal Sequencing

The N-terminal amino acid sequence of the enzyme was: SSCSPEVFSSVGIPKGEVL (SEQ ID NO:3).

Example 5

Cloning of the Gene Encoding the Enzyme from *Myrothecium* sp. Strain

Fungal Strain and its Growth

*Myrothecium* sp. strain was grown at 25° C., 165 rpm for 7 days in YS medium. The mycelium was harvested by centrifugation at 7000 rpm for 30 minutes. The harvested mycelium was stored at −80° C. before use for RNA extraction.

Extraction of Total RNA

Total RNA was extracted from 100 mg mycelium using the RNeasy Mini Kit.

Degenerate Primers

The following degenerate primers were designed based on part of the N-terminal amino acid sequence, SSCSPEVFSS-VGIPKGEVL: 5' end degenerate primer KD60II (gTC ggC AT(T/C) CCN AA(A/g) ggN gA) (SEQ ID NO:4) and used for PCR amplification.

Cloning of the Enzyme Gene:

The 3' RACE Kit was used to synthesize the cDNA from *Myrothecium* sp. strain. About 5 mg total RNA was used as a template and the Adapter Primer was used to synthesize the first strand of cDNA. Then the cDNA was PCR-amplified using the above degenerate primers. The PCR reaction system and conditions were as follows:

| | |
|---|---|
| 10 x PCR buffer | 5 µl |
| 25 mM MgCl$_2$ | 3 µl |
| 10 mM dNTP mix | 1 µl |
| 5'Primer (KD60II; 10 µM) | 1 µl |
| AUAP (10 µM) | 1 µl |
| Taq DNA polymerase | 0.5 µl |
| cDNA synthesis reactant | 2 µl |
| Add autoclaved, distilled water to | 50 µl |

PCR Conditions

PCR program: 94° C. for 3 mins; 30 cycles of 94° C. for 40 secs, 55° C. for 40 secs and 72° C. for 1.5 min; final extension at 72° C. for 10 mins After running RT-PCR amplification using 3' RACE (Rapid Amplification of cDNA End) kit in which a 3' end specific primer (AUAP) is used, gel analysis of the PCR product revealed a specific band corresponding to a fragment of about 1600 bp was obtained. The products were recovered from 1% LMP agarose gel, purified by incubation in a 70° C. bath, followed by using the PCR Preps DNA Purification System. The concentrations of purified products were determined by measuring the absorbance of $A_{260}$ and $A_{280}$ in a spectrophotometer. Then these purified fragments were ligated to the pGEM-T Vector using the corresponding Promega Kit:

| | |
|---|---|
| T4 DNA Ligase 2XBuffer | 1 µl |
| pGEM-T Vector (50 ng) | 1 µl |
| PCR product | 40 ng |
| T4 DNA Ligase (3 Weiss units/µl) | 1 µl |
| dH$_2$O to a final volume of | 10 µl |

The reactions were incubated overnight at 4° C. 2-4 µl of the ligation products were transformed into 50 µl JM109 high efficiency competent cells by the "heat shock" method (J. Sambrook, E. F. Fritsch, T. Maniatis (1989) Molecular Cloning 1.74, 1.84). Transformation cultures were plated onto LB plates with ampicillin/IPTG/X-Gal, and these plates were incubated overnight at 37° C. Recombinant clones were identified by colour screening on indicator plates and colony PCR screening as follows:

Colony PCR System:

| | |
|---|---|
| 10 x PCR buffer | 5 µl |
| 25 mM MgCl$_2$ | 3 µl |
| 10 mM dNTP mix | 1 µl |
| 5'Primer (10 µM, KD60II) | 2 µl |
| AUAP (10 µM) | 2 µl |
| TaqDNA polymerase | 0.5 µl |
| Add autoclaved, distilled water to | 50 µl |

Dip a white colony with a tip and pipet the colony into PCR mixture as the template.

PCR Conditions

PCR program: 94° C. for 3 mins; 30 cycles of 94° C. for 40 secs, 55° C. for 40 secs and 72° C. for 1.5 min; final extension at 72° C. for 10 mins.

The positive clones were inoculated into 3 ml LB Ampicillin liquid medium and incubated overnight at 37° C. with shaking (about 250 rpm). Cells were pelleted by centrifugation for 5 min at 10,000×g, and plasmid samples were prepared from the cell pellet by using Minipreps DNA Purification System. Finally, the plasmids were sequenced using the BigDye Terminator Cycle Sequencing Ready Reaction Kit and the ABI377 sequencer. The sequencing reaction was as follows:

| | |
|---|---|
| Terminator Ready Reaction Mix | 8 μl |
| Plasmid DNA | 1.0-1.5 μg |
| Primer | 3.2 pmol |
| dH₂O to a final volume of | 10 μl |

Sequence analysis of the cDNA clone showed that the sequence contained coding region for the mature peptide.

Cloning of the 5' End of the Target Gene

In order to get the full length sequence of the target gene, new primers for 5' end cloning by using DNA Walking™ SpeedUp Kit (See Gene, Cat. No. #K1502) were designed. And the genomic DNA was extracted with the DNeasy Plant Mini Kit from the mycelium used for RNA preparation.

```
Esterase as1:
                                    (SEQ ID NO: 5)
5' CCA CTC CAG GTT GTG GAA GCA AC 3'

Esterase as2:
                                    (SEQ ID NO: 6)
5' CAG CCG TTC CAG TAC GAG TAT TC 3'

Esterase as3:
                                    (SEQ ID NO: 7)
5' CGA AGC GAC CAT TCC AGT CCT CGA 3'
```

PCR Condition
1st PCR

| | |
|---|---|
| 10 x PCR buffer | 5 μl |
| 25 mM MgCl₂ | 3 μl |
| 10 mM dNTP mix | 1 μl |
| 10 μM Esterase as1 | 1 μl |
| 2.5 uM DW-ACP 1~4 (provided by the kit) | 4 μl |
| genomic DNA | 1 ul |
| Taq DNA polymerase | 0.5 μl |
| Add autoclaved, distilled water to | 50 μl |

Conditions: 94° C. for 3 mins; 30 cycles of 94° C. for 45 secs, 55° C. for 45 secs and 72° C. for 1 mins; final extension at 72° C. for 10 mins.
2nd PCR

| | |
|---|---|
| 10 x PCR buffer | 5 μl |
| 25 mM MgCl₂ | 3 μl |
| 10 mM dNTP mix | 1 μl |
| 10 μM Esterase as3 | 1 μl |
| 10 μM universal primer (provided by the kit) | 1 μl |
| 20x diluted 1st PCR solution | 1 ul |
| Taq DNA polymerase | 0.5 μl |
| Add autoclaved, distilled water to | 50 μl |

Conditions: 94° C. for 3 mins; 30 cycles of 94° C. for 45 secs, 55° C. for 45 secs and 72° C. for 1 mins; final extension at 72° C. for 10 mins.

A 300 bp fragment was obtained and confirmed to be the 5' end of the gene including the start codon ATG.

Primers for full length cloning were designed as:

```
Esterase s01:
                                    (SEQ ID NO: 8)
5' ATG CAA TCG CCG TTA GTA AAA GTC 3'

Esterase as00:
                                    (SEQ ID NO: 9)
5' TCT AGG CTT GCC CAT TCG CTC CTA 3'
```

| | |
|---|---|
| 10x pfu DNA polymerase buffer | 5 μl |
| 15 mM MgSO4 | 4 μl |
| 10 mM dNTP | 1 μl |
| 10 μM s01 | 1 μl |
| 10 μM as00 | 1 μl |
| genomic DNA | 2 μl |
| pfu DNA polymerase | 1 μl |

Conditions: 94° C. for 3 mins; 30 cycles of 94° C. for 45 secs, 50° C. for 40 secs and 72° C. for 2 mins; final extension at 72° C. for 10 mins.

A fragment around 2 kb was obtained and confirmed to be the target gene. It contained two introns either predicted by Agene or by alignment with the coding region for mature peptide. The introns were removed by using overlap extension PCR. Primers for intron removing were designed as:

```
Esterase jumpas1:
                                    (SEQ ID NO: 10)
5' TCC TGT CGA ACA GCC GTT CCA GTA CGA GTA TTC

TTG 3'

Esterase jumps1:
                                    (SEQ ID NO: 11)
5' TAC TCG TAC TGG AAC GGC TGT TCG ACA GGA GGA

CGT CA 3'

Esterase jumpas2:
                                    (SEQ ID NO: 12)
5' GGA TGG GTA ATA GTC CAA TGA TCT CAT GGT CAG

AAT G 3'

Esterase jumps1:
                                    (SEQ ID NO: 13)
5' ACC ATG AGA TCA TTG GAC TAT TAC CCA TCC AAC

TGC GA 3'
```

Three individual PCR reactions were performed separately by using esterase s01 with jumpas2, jumps1 with jumpas1 and jumps2 with as00. Three fragments of size at 500 bp (fragment I), 150 bp (fragment II) and 1100 bp (fragment III) were resulted accordingly. PCR fragments were purified by PCR Preps DNA Purification System (Promega, Cat. No. A7170).

Overlap extension PCR was performed as below:

| 1st PCR without primers | |
|---|---|
| 10x pfu DNA polymerase buffer | 5 μl |
| 25 mM MgSO4 | 4 μl |
| 10 mM dNTP | 1 μl |
| Fragment I + II + III | 1 + 1 + 1 μl |
| Pfu DNA polymerase | 1 μl |
| H₂O | 34 μl |

Conditions: 94° C. for 3 mins; 4 cycles of 94° C. for 40 secs, 37° C. for 1 min and 72° C. for 2 mins; left on ice till the 2nd PCR was performed with the addition of 1 μl of 10 μM esterase s01 and as00 each to the PCR solution and the program was 94° C. for 2 mins; 25 cycles of 94° C. for 40 secs, 50° C. for 40 secs and 72° C. for 2 mins; final extension at 72° C. for 10 mins.

A fragment at ~1.5 kb was obtained. The full length sequence was as below (SEQ ID No. 1). The deduced amino acid sequence was SEQ ID NO: 2. Position 1-20 of SEQ ID No. 2 was identified as the signal by SignalP, 21-39 was the n-terminal sequence of the enzyme (SEQ ID No. 1) and 21-520 was the mature peptide. The full length fragment was cloned into the pGEM-T vector and transformed into the ElectroMax™ DH10B competent cell by electroporation. The positive clone was sequencing confirmed and deposited in DSMZ as DSM19428 (DSMZ-Deutsche Sammlung von Mikroorganismen and Zellkulturen GmbH, Mascheroder Weg 1b, D-38124 Braunschweig, Germany).

Example 6

Expression of *Myrothecium* Esterase of SEQ ID NO: 2 in *Aspergillus*

Strains and Plasmids
*E. coli* DH12S (Gibco BRL) and *E. coli* DB6507 (available from ATCC with the number ATCC35673) (F⁻, pyrF74::Tn5, supE44, lacY1, ara14, galK2, xyl5, leuB6, proA2, hsdS20, recA13, rpsL20, thi1, lambda⁻) were used for the plasmid construction. *E. coli* DB6507 was especially used for the amplification of pJaL721 and its deliveries. The plasmid pJaL721 is described in WO10170204. *Aspergillus oryzae* BECh2 (described in WO00/39322) was used for the expression of enzyme gene.
Media
LB was used for the cultivation of *E. coli*. SC-glucose was used for the cultivation of *S. cerevieiae*.

| LB | |
|---|---|
| Bacto Tryptone | 1% |
| NaCl | 1% |
| Bacto Yeast ext | 0.5% | pH 7.0

| SC-glucose | |
|---|---|
| 20% glucose* | 100 ml/L |
| 5% threonine* | 4 ml/L |
| 1% tryptophan* | 10 ml/L |
| 20% casamino acids* | 25 ml/L |
| 10 X basal solution* | 100 ml/L |
| Agar | 20 g/L |

*Filter sterilized separately
(Final pH around 5.6)

| 10X Basal solution | |
|---|---|
| yeast nitrogen base w/o amino acids | 66.8 g/L |
| succinate | 100 g/L |
| NaOH | 60 g/L |

Medium for *Aspergillus* Transformation
COVE
 342.3 g/L sucrose
 20 ml/L COVE salt solution
 10 mM acetamide
 30 g/L noble agar COVE II
 30 g/L sucrose
 20 ml/L COVE salt solution
 10 mM, acetamide
 30 g/L noble agar
COVE-N-gly
 218 g/L sorbitol
 10 g/L glucose
 2.02 g/L KNO$_3$
 50 ml/L COVE salt solution
 25 g/L noble agar
 10 g/L glycerol pH5.2
COVE Salt Solution
 26 g KCl
 26 g MgSO$_4$.7 aq
 76 g KH$_2$PO$_4$,
 50 ml Cove trace metals/L
COVE Trace Metals
 0.04 g NaB$_4$O$_7$.10 aq
 0.4 g CuSO$_4$.5 aq
 1.2 g FeSO$_4$.7 aq
 0.7 g MnSO$_4$.aq
 0.7 g Na$_2$MoO$_2$.2 aq
 0.7 g ZnSO$_4$.7 aq/L
COVE Top Agarose
 342.3 g/L sucrose
 20 ml/L COVE salt solution
 10 mM acetamide
 10 g/L low-melt agarose
SF medium (100 ml/SF) for *Aspergillus*:
MS-9
 30 g/L soybean powder
 20 g/L glycerol pH 6.0
MDU-2 Bp FuPE
 45 g/L malto dexstrin
 7 g/L yeast extract
 12 g/L KH$_2$PO$_4$
 0.75 g/L NH$_4$Cl
 1 g/L MgSO$_4$.7H$_2$O
 2 g/L K$_2$SO$_4$
 1 g/L NaCl
 0.5 ml/L AMG trace metal solution pH 6.0
AMG metal solution: Citric acid 1 aq 12 g/l, ZnSO$_4$ 7 aq 57 g/l, CuSO$_4$ 5 aq 10 g/l, NiCl$_2$ 6 aq 2 g/l, FeSO$_4$ 7 aq 55 g/l, MnSO$_4$ 5 aq 46.6 g/l.
YPG medium: 4 g/L yeast extract, 1 g/L KH$_2$PO$_4$, 0.5 g/L MgSO$_4$.7 aq, 15 g/L glucose, pH 6.0
STC buffer: 0.8 M sorbitol, 50 mM Tris pH 8, 50 mM CaCl$_2$
STPC buffer: 40% PEG4000 in STC buffer
Construction of Expression Plasmids for *Aspergillus* and its Expression in *Aspergillus oryzae*
To express the *Myrothecium* esterase gene in *Aspergillus*, the expression plasmid was constructed. The cDNA clone of esterase gene was amplified by PCR using the plasmid in the deposited strain DSM19428 as template and the Primer Ori F (SEQ ID NO:14) and Primer Ori R (SEQ ID NO:15) to introduce the restriction enzyme sites, BamHI and XhoI.

```
Primer Ori.F;
5'-CAACTGGGGATCCACCATGCAATCGCCGTTAG-3'
          BamHI

Primer Oi.R;
5'-CAAAACCGGCTCGAGCTCATGACACTCGAAAGAAGAAG-3'
              XhoI
```

PCR Condition

|   | Temp. (° C.) | Time (min) | High Fidelity PCR Master Kit (Roche) | | |
|---|---|---|---|---|---|
| 1 | 94 | 2:00 | Total volume | 50 | μl |
| 2 | 94 | 0:40 | Template | 0.3 | μl |
| 3 | 55 | 0:40 | Primer 100 pmol/μl F | 0.5 | μl |
| 4 | 72 | 1:30 | Primer 100 pmol/μl R | 0.5 | μl |
|   | go to 2 | 29 times | Polymerase Mix | 25 | μl |
| 5 | 72 | 7:00 | H$_2$O (PCR grade) | 23.7 | μl |

The amplified 1.6 kb fragment was digested with BamHI and XhoI, and ligated into the expression plasmid pJaL721 (WO10170204) digested with the same restriction enzymes. The resulting plasmid was designated as pJal721-ogrinal esterase.

The plasmid was transformed into *A. oryzae* BECh2 and transformants were isolated as described in WO02/20730.

*Aspergillus oryzae* strain BECh2 was inoculated in 100 ml of YPG medium and incubated at 32° C. for 16 hours with stirring at 80 rpm. Grown mycelia was collected by filtration followed by washing with 0.6 M KCl and re-suspended in 30 ml of 0.6 M KCl containing Glucanex® (Novozymes) at the concentration of 30 μl/ml. The mixture was incubated at 32° C. with the agitation at 60 rpm until protoplasts were formed. After filtration to remove the remained mycelia, protoplasts were collected by centrifugation and washed with STC buffer twice. The protoplasts were counted with a hematitometer and re-suspended in a solution of STC:STPC:DMSO (8:2:0.1) to a final concentration of 1.2×10$^7$ protoplasts/ml. About 4 μg of DNA was added to 100 μl of protoplast solution, mixed gently and incubated on ice for 30 minutes. 1 μl STPC buffer was added to the mixture and incubated at 37° C. for another 30 minutes. After the addition of 10 ml of Cove top agarose pre-warmed at 50° C., the reaction mixture was poured onto COVE agar plates. The plates were incubated at 32° C. for 5 days.

Appeared transformants were isolated on COVE-II and used for the cultivation in shaking flask.

The strains were cultivated in MS-9 medium for 1 day as the seed cultivation, then transferred into MDU-2 Bp FuPE medium for enzyme production. The culture broth was used for the enzymatic assay (pNPB assay). As the results, some of obtained transformants showed significantly higher activities than the others. It was confirmed on SDS-PAGE (12.5% SDS-poly acrylamide gel electrophoresis at 20 mA for 0.5 hr, and stained with SYPRO Orange) that these transformants secreted high amount of esterase, while the equivalent protein was not secreted from the used host strain BECh2.

Example 7

In Vitro Digestion Test of Esterase

Esterase (SEQ ID NO:2) was expressed in and excreted from *Aspergillus oryzae* according to example 6. The performance of the purified esterase was tested in this example. The purpose of the current study was to investigate the efficacy of xylanases in combination with an esterase as regards solubilisation of non starch polysaccharides (NSP). The esterase mentioned in the example refers to the esterase of SEQ ID NO:2.

Xylanases

The following enzymes were tested:

The RONOZYME WX xylanase, a known monocomponent animal feed xylanase derived from *Thermomyces lanuginosus* and commercially available from DSM Nutritional Products, Wurmisweg 576, CH-4303 Kaiseraugst, Switzerland (this xylanase is also described in WO 96/23062);

The Shearzyme 500 xylanase, a monocomponent xylanase derived from *Aspergillus aculeatus* and commercially available from Novozymes A/S, Bagsvaerd, Denmark.

The study was focused on quantification of the total arabinoxylan (sum of arabinose and xylose) content after in vitro incubation in a procedure mimicking the gastric and small intestinal digestion steps in monogastric digestion. In the in vitro system up to 15 test tubes, containing a substrate of interest, were incubated with HCl/pepsin (simulating gastric digestion), and subsequently with pancreatin (simulating intestinal digestion). Three test tubes were used for each treatment included. At the end of the intestinal incubation phase samples of the in vitro digesta were removed and analysed for insoluble fibre polysaccharides.

An outline of the in vitro procedure is shown in Table 2 in which pH and temperature indicate the respective set points (target values).

TABLE 2

Outline of in vitro digestion procedure

| Components added | pH | Temperature | Time course | Simulated digestion phase |
|---|---|---|---|---|
| 0.8 g substrate, 4.1 ml HCl-1 (0.072M) | 3.0 | 40° C. | t = 0 min | Mixing |
| 0.5 ml HCl-2 (0.072M)/ pepsin (3000 U/g substrate), 0.1 ml enzyme solution | 3.0 | 40° C. | t = 30 min | Gastric digestion |
| 0.9 ml NaOH (0.16M) | 6.8 | 40° C. | t = 1.5 hours | Intestinal digestion |
| 0.4 ml NaHCO$_3$ (1M)/ pancreatin (8 mg/g diet) | 6.8 | 40° C. | t = 2.0 hours | Intestinal digestion |
| Terminate incubation | 6.8 | 40° C. | t = 6.0 hours | |

Conditions

Substrate: 0.7 g maize (milled to pass a 0.5 mm screen), 0.3 g soy bean meal, provided as a premixed diet pH: stomach step=pH 3.0/intestinal step=pH 6.8 (towards the termination of the incubation the pH may rise to 7.0)

HCl: 0.072 M for 1.5 hours (i.e. 30 min HCl-substrate pre-mixing)

pepsin: 3000 U/g diet for 1 hour (Sigma P-7000)

pancreatin: 8 mg/g diet for 4 hours (Sigma P-7545)

temperature: 40° C.

Replicates: 3

Solutions Used for the In Vitro Incubation

HCl-1: 0.072 M HCl containing Ca$^{2+}$

Make 500 mL: 3676 mg CaCl$_2$.2H$_2$O and 36 mL 1M HCl, fill with de-ionised water (CaCl$_2$.2H$_2$O=5 mM*0.5 L*147.02 g/mol=367.55 mg CaCl$_2$.2H$_2$O)

HCl-2: HCl/pepsin:

Make same day

Make 100 mL: Weigh out 1.06 g pepsin, fill with HCl-1.

0.16 M NaOH:

Make 100 mL: 16 mL 1M NaOH, fill with de-ionised water.

Pancreatin dissolved in 1 M NaHCO$_3$ containing 8 mg pancreatin/g diet:

NaHCO$_3$-pancreatin is pre made, divided into portions and frozen. It is slowly thawed in refrigerator over night before use.

Sodium acetate buffer for enzyme additions and washing in the fibre analysis procedures:
Acetate buffer, 0.1 M, pH 5.
Solution A: 0.2 M acetic acid:
2.85 ml acetic acid and 250 mL with milliQ water.
Solution B: 0.2 M sodium acetate:
13.6 g sodium acetate trihydrate and 500 mL with milliQ water.
100 mM Buffer:
148 mL solution A
352 mL solution B
735 mg $CaCl_2.2H_2O$
approx. 400 ml milliQ water
Check that pH is 5.0, if not adjust.
Fill to 1000 mL with de-ionised water.

Enzyme Protein Determinations

The amount of enzyme protein (EP) concentration for the purified esterase was calculated on the basis of the $A_{280}$ values and the amino acid sequences (amino acid compositions) using the principles outlined in S. C. Gill & P. H. von Hippel, Analytical Biochemistry 182, 319-326, (1989).

Experimental Procedure for In Vitro Model

The experimental procedure was according to the above outline. pH was measured at time 1, 2.5, and 5.5 hours. Incubations were terminated after 6 hours and samples were removed and placed on ice before centrifugation (10000×g, 10 min, 4° C.). Supernatants were discarded and the pellet residue washed once with a sodium acetate buffer (pH 5 and 100 mM).

Analysis

The analysis of remaining fibre polysaccharides was made according to Theander et al (1995): Total dietary fiber determined as neutral sugar residues, uronic acid residues, and Klason lignin (the Uppsala method): Collaborative study, in J. AOAC Int. vol. 78, no. 4, pp. 1030-1044, except that cellulose was not analysed in the present example. In brief, the starch in the sample is removed by an enzyme digestion procedure with alpha-amylase and amyloglucosidase. Soluble polymers are precipitated at 80% aqueous ethanol concentration.

Precipitated and insoluble polysaccharides are hydrolysed for 55 minutes at 125° C. in 0.4 M sulphuric acid together with an internal standard (myo-Inositol) Released neutral sugars are quantified by gas-liquid chromatography as alditol acetates and their content calculated relative to the internal standard and taking the original sample weight into account.

Xylanolytic Activity

The xylanolytic activity can be expressed in FXU-units, determined at pH 6.0 with remazol-xylan (4-O-methyl-D-glucurono-D-xylan dyed with Remazol Brilliant Blue R, Fluke) as substrate.

A xylanase sample is incubated with the remazol-xylan substrate. The background of non-degraded dyed substrate is precipitated by ethanol. The remaining blue colour in the supernatant (as determined spectrophotometrically at 585 nm) is proportional to the xylanase activity, and the xylanase units are then determined relatively to an enzyme standard at Vs standard reaction conditions, i.e. at 50.0° C., pH 6.0, and 30 minutes reaction time.

Table 3 below shows the fresh weight content (%) of insoluble arabinoxylan (sum of arabinose and xylose) residues in the feed after the in vitro incubation with the various xylanase and esterase treatments. The control is without added enzymes.

TABLE 3

| Treatment | Arabinoxylan content (%) (±Standard deviation) |
|---|---|
| Control, no enzyme treatment, 0.1 ml buffer added | 3.97[a] (±0.125) |
| RONOZYME WX + Shearzyme (10000 + 10000 FXU/kg diet) via 0.1 ml buffer | 3.85[a] (±0.015) |
| RONOZYME WX + Shearzyme (10000 + 10000 FXU/kg diet) via 0.1 ml buffer + Myrothecium esterase at 5 mg EP/kg diet, via 0.1 ml buffer | 3.63[b] (±0.095) |
| RONOZYME WX + Shearzyme (1000 + 1000 FXU/kg diet) via 0.1 ml buffer + Myrothecium esterase at 5 mg EP/kg diet via 0.1 ml buffer | 3.56[b] (±0.207) |
| Myrothecium esterase at 5 mg EP/kg diet via 0.1 ml buffer | 3.95[a] (±0.099) |

[a,b]Means within a column not sharing a common letter superscript differ with statistical significance (P < 0.05).

It appears from Table 3 that, surprisingly, the addition of the esterase from Myrothecium results in a statistically significant reduction in the insoluble arabinoxylan fraction, i.e. a solubilisation. By adding the esterase the xylanase dose may be reduced up to 10 times while still obtaining a statistically significant reduction in the content of insoluble rabinoxylans.

Deposit of Biological Material

The following biological material has been deposited under the terms of the Budapest Treaty with the DSMZ-Deutsche Sammlung von Mikroorganismen und Zellkulturen GmbH (DSM), Mascheroder Weg 1 B, D-38124 Braunschweig, Germany, and given the following accession number:

| Deposit | Accession Number | Date of Deposit |
|---|---|---|
| Escherichia coli | DSM19428 | 14th June 2007 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application or its progeny are filed. However, it should be understood that the availability of a deposit does not constitute a license to practice the subject invention in derogation of patent rights granted by governmental action.

The invention claimed is:

1. An isolated polypeptide having feruloyl esterase activity, wherein the polypeptide is selected from the group consisting of:
  (a) a polypeptide comprising an amino acid sequence having at least 95% sequence identity to the mature polypeptide of amino acids 21 to 520 of SEQ ID NO: 2; and
  (b) a polypeptide encoded by a polynucleotide comprising a nucleotide sequence that hybridizes under at least very high stringency conditions with (i) the nucleotide sequence of nucleotides 61 to 1560 of SEQ ID NO: 1, (ii) a cDNA sequence contained in the nucleotide sequence of nucleotides 61 to 1560 of SEQ ID NO: 1, or (iii) a full-length complementary strand of (i) or (ii), wherein very high stringency conditions are defined as prehybridization and hybridization at 42° C. in 5×SSPE, 0.3% SDS, 200 micrograms/ml sheared and denatured salmon sperm DNA, and 50% formamide following standard Southern blotting procedures for 12 to 24 hours optimally, and washing three times each for 15 minutes using 2×SSC, 0.2% SDS at 70° C.

2. The isolated polypeptide of claim 1, which has at least 97% identity to the mature polypeptide of amino acids 21 to 520 of SEQ ID NO: 2.

3. The isolated polypeptide of claim 1, which has at least 98% identity to the mature polypeptide of amino acids 21 to 520 of SEQ ID NO: 2.

4. The isolated polypeptide of claim 1, which has at least 99% identity to the mature polypeptide of amino acids 21 to 520 of SEQ ID NO: 2.

5. The isolated polypeptide of claim 1, comprising or consisting of the amino acid sequence of SEQ ID NO: 2.

6. The isolated polypeptide of claim 1, comprising or consisting of the mature polypeptide of amino acids 21 to 520 of SEQ ID NO: 2.

7. A nucleic acid construct comprising a nucleotide sequence that encodes the polypeptide of claim 1, wherein the nucleotide sequence is operably linked to one or more heterologous control sequences that direct the production of the polypeptide in a suitable expression host.

8. A recombinant expression vector comprising the nucleic acid construct of claim 7.

9. A recombinant host cell comprising the nucleic acid construct of claim 7.

10. A method for producing a polypeptide, the method comprising (a) cultivating the recombinant host cell of claim 9 to produce a supernatant comprising the polypeptide; and (b) recovering the polypeptide.

11. A method for improving the nutritional value of an animal feed, wherein at least one polypeptide of claim 1 is added to the animal feed.

12. A composition comprising at least one polypeptide of claim 1, and
  (a) at least one fat soluble vitamin, and/or
  (b) at least one water soluble vitamin, and/or
  (c) at least one trace mineral.

13. The composition of claim 12, which further comprises amylase, phytase, xylanase, galactanase, alpha-galactosidase, protease, phospholipase, beta-glucanase, and/or arabinofuranosidase.

14. An animal feed composition comprising the polypeptide of claim 1.

15. A method for improving the nutritional value of an animal feed, the method comprising adding the polypeptide of claim 1 to the feed.

* * * * *

SEQUENCE LISTING

```
<160> NUMBER OF SEQ ID NOS: 15

<210> SEQ ID NO 1
<211> LENGTH: 1684
<212> TYPE: DNA
<213> ORGANISM: Myrothecium sp.
<220> FEATURE:
```

```
<221> NAME/KEY: sig_peptide
<222> LOCATION: (1)..(60)
<220> FEATURE:
<221> NAME/KEY: CDS
<222> LOCATION: (1)..(1560)

<400> SEQUENCE: 1 atg caa tcg ccg tta gta aaa gtc ctt atg gca tcg act gcc gcc cag      48
Met Gln Ser Pro Leu Val Lys Val Leu Met Ala Ser Thr Ala Ala Gln
1               5                   10                  15 gtt gtt caa gct tcg agt tgt tcc cca gaa gtc ttc tca tct gtc ggg      96
Val Val Gln Ala Ser Ser Cys Ser Pro Glu Val Phe Ser Ser Val Gly
                20                  25                  30 att ccc aaa ggc gaa gtt ctg tct ctg acg gct gag ctc gcg gaa act     144
Ile Pro Lys Gly Glu Val Leu Ser Leu Thr Ala Glu Leu Ala Glu Thr
            35                  40                  45 ctc cca tcg caa caa acg gcg aac aat tgg ccc atc ttc tcc aac acg     192
Leu Pro Ser Gln Gln Thr Ala Asn Asn Trp Pro Ile Phe Ser Asn Thr
        50                  55                  60 acg act ctg act tgc cag gtc acg atc cag tac acc cat ccg gga tgg     240
Thr Thr Leu Thr Cys Gln Val Thr Ile Gln Tyr Thr His Pro Gly Trp
65                  70                  75                  80 aac gac acc atc aac acc tac gtg tgg ctt ccc gtc gag gac tgg aat     288
Asn Asp Thr Ile Asn Thr Tyr Val Trp Leu Pro Val Glu Asp Trp Asn
                85                  90                  95 ggt cgc ttc gtc ggt gtc ggt gga gga tgg gca gca ggc cag ccg         336
Gly Arg Phe Val Gly Val Gly Gly Gly Trp Ala Ala Gly Gln Pro
                100                 105                 110 act gat ctg ggt ctc cag gtg gcc aga gga tac gct gcc gtt acc acg     384
Thr Asp Leu Gly Leu Gln Val Ala Arg Gly Tyr Ala Ala Val Thr Thr
            115                 120                 125 gac ggt ggt cat cct ttt gag cgc tct gat gac ctg gat tac tgg gcc     432
Asp Gly Gly His Pro Phe Glu Arg Ser Asp Asp Leu Asp Tyr Trp Ala
        130                 135                 140 atg gtg ggg aaa gac agc atc aat tgg tac aat atg ctg aat ttc ttc     480
Met Val Gly Lys Asp Ser Ile Asn Trp Tyr Asn Met Leu Asn Phe Phe
145                 150                 155                 160 tcc gtg gcc cta gac gat gca gct aca ttg ggc aag gca gcc gtt gtc     528
Ser Val Ala Leu Asp Asp Ala Ala Thr Leu Gly Lys Ala Ala Val Val
                165                 170                 175 gcc tac tat gga cga gaa caa gaa tac tcg tac tgg aac ggc tgt tcg     576
Ala Tyr Tyr Gly Arg Glu Gln Glu Tyr Ser Tyr Trp Asn Gly Cys Ser
                180                 185                 190 aca gga gga cgt caa ggc ttc atg atg gcc cag aga tac cca gaa cag     624
Thr Gly Gly Arg Gln Gly Phe Met Met Ala Gln Arg Tyr Pro Glu Gln
            195                 200                 205 tac gat ggc att ctc gcc tct gcg ccc gcc att aac tgg ggc cag ctg     672
Tyr Asp Gly Ile Leu Ala Ser Ala Pro Ala Ile Asn Trp Gly Gln Leu
        210                 215                 220 gtc atc agc atg tac ttg ccc att ctg acc atg aga tca ttg gac tat     720
Val Ile Ser Met Tyr Leu Pro Ile Leu Thr Met Arg Ser Leu Asp Tyr
225                 230                 235                 240 tac cca tcc aac tgc gag ctc aat gct att aca agc gct gct gtt gaa     768
Tyr Pro Ser Asn Cys Glu Leu Asn Ala Ile Thr Ser Ala Ala Val Glu
                245                 250                 255 gca tgt gat gaa gct gac ggt ctg aag gac gac gta gtt gtg cgg aca     816
Ala Cys Asp Glu Ala Asp Gly Leu Lys Asp Asp Val Val Val Arg Thr
                260                 265                 270 tgg gag tgc gaa ttc gat gct tcg agc gtc gtc ggc cag aag tac agc     864
Trp Glu Cys Glu Phe Asp Ala Ser Ser Val Val Gly Gln Lys Tyr Ser
            275                 280                 285
```

```
tgc gga aac gag tct ggt atc atc acc tcc cag gct gcc gag gtt gct    912
Cys Gly Asn Glu Ser Gly Ile Ile Thr Ser Gln Ala Ala Glu Val Ala
        290                 295                 300 tcc aca acc tgg agt ggc tcc gtc ttc cag aac ggc cga cgt gct gga    960
Ser Thr Thr Trp Ser Gly Ser Val Phe Gln Asn Gly Arg Arg Ala Gly
305                 310                 315                 320 tgg gga ctt gct cca tcg gct ccc ttg gtt ggc att gct aac gtt gtt   1008
Trp Gly Leu Ala Pro Ser Ala Pro Leu Val Gly Ile Ala Asn Val Val
                325                 330                 335 tgc tcc tcg ccc ggt gat tgt gaa ccg gca ccc ttc atc ctc tca acc   1056
Cys Ser Ser Pro Gly Asp Cys Glu Pro Ala Pro Phe Ile Leu Ser Thr
            340                 345                 350 caa tgg atc tcc aag ttc gtt ctt gag aac agc gat gcg gac ctc tcc   1104
Gln Trp Ile Ser Lys Phe Val Leu Glu Asn Ser Asp Ala Asp Leu Ser
        355                 360                 365 acc ctt acg gac gag gag tat ctc agc ctc ttc cgc caa tcg gcc aac   1152
Thr Leu Thr Asp Glu Glu Tyr Leu Ser Leu Phe Arg Gln Ser Ala Asn
370                 375                 380 aag tac agc tca ctc tcc gac acg aac gat ccg gat ctg acc gac ttc   1200
Lys Tyr Ser Ser Leu Ser Asp Thr Asn Asp Pro Asp Leu Thr Asp Phe
385                 390                 395                 400 aag ttg gcc ggc ggc aag atg att aca tgg cac ggc ggc gac gat atc   1248
Lys Leu Ala Gly Gly Lys Met Ile Thr Trp His Gly Gly Asp Asp Ile
                405                 410                 415 ctc att cca tac aac agt acc gtc gat tac tac gag aaa gtt gct gca   1296
Leu Ile Pro Tyr Asn Ser Thr Val Asp Tyr Tyr Glu Lys Val Ala Ala
            420                 425                 430 ctg gac gca gac gtc ttg gac tac ttc aga ttc ttc tca gcg ccc gga   1344
Leu Asp Ala Asp Val Leu Asp Tyr Phe Arg Phe Phe Ser Ala Pro Gly
        435                 440                 445 gtt cag cac tgc cag gac gga gct ggg tgg ttc ccc ggt gag gcg ttt   1392
Val Gln His Cys Gln Asp Gly Ala Gly Trp Phe Pro Gly Glu Ala Phe
        450                 455                 460 gag tcc ctg gtc gac tgg gtt gag aat ggc aaa gct cca gag acg ctg   1440
Glu Ser Leu Val Asp Trp Val Glu Asn Gly Lys Ala Pro Glu Thr Leu
465                 470                 475                 480 tat ggc agg cct cgt ggt agc aac ttc act gga gag aga gaa gcc aac   1488
Tyr Gly Arg Pro Arg Gly Ser Asn Phe Thr Gly Glu Arg Glu Ala Asn
                485                 490                 495 ttg tgc ctg tat ccc aag cag atc cgt tac att ggg gga gac ccg gag   1536
Leu Cys Leu Tyr Pro Lys Gln Ile Arg Tyr Ile Gly Gly Asp Pro Glu
            500                 505                 510 gtt gct tct tct ttc gag tgt cag tgagaaactg ccggttttgt caaggcagag   1590
Val Ala Ser Ser Phe Glu Cys Gln
        515                 520 aagaattggg caagttcatg tctccttatc tcattgacac gaaatagtag gcagtattgg   1650
ttgcgaacaa ataggagcga atgggcaagc ctag                               1684

<210> SEQ ID NO 2
<211> LENGTH: 520
<212> TYPE: PRT
<213> ORGANISM: Myrothecium sp.

<400> SEQUENCE: 2

Met Gln Ser Pro Leu Val Lys Val Leu Met Ala Ser Thr Ala Ala Gln
1               5                   10                  15

Val Val G

```
Leu Pro Ser Gln Gln Thr Ala Asn Asn Trp Pro Ile Phe Ser Asn Thr
    50                  55                  60
Thr Thr Leu Thr Cys Gln Val Thr Ile Gln Tyr Thr His Pro Gly Trp
65              70                  75                  80
Asn Asp Thr Ile Asn Thr Tyr Val Trp Leu Pro Val Glu Asp Trp Asn
                85                  90                  95
Gly Arg Phe Val Gly Val Gly Gly Gly Trp Ala Ala Gly Gln Pro
                100                 105                 110
Thr Asp Leu Gly Leu Gln Val Ala Arg Gly Tyr Ala Ala Val Thr Thr
            115                 120                 125
Asp Gly Gly His Pro Phe Glu Arg Ser Asp Asp Leu Asp Tyr Trp Ala
    130                 135                 140
Met Val Gly Lys Asp Ser Ile Asn Trp Tyr Asn Met Leu Asn Phe Phe
145                 150                 155                 160
Ser Val Ala Leu Asp Asp Ala Ala Thr Leu Gly Lys Ala Ala Val Val
                165                 170                 175
Ala Tyr Tyr Gly Arg Glu Gln Glu Tyr Ser Tyr Trp Asn Gly Cys Ser
                180                 185                 190
Thr Gly Gly Arg Gln Gly Phe Met Met Ala Gln Arg Tyr Pro Glu Gln
            195                 200                 205
Tyr Asp Gly Ile Leu Ala Ser Ala Pro Ala Ile Asn Trp Gly Gln Leu
    210                 215                 220
Val Ile Ser Met Tyr Leu Pro Ile Leu Thr Met Arg Ser Leu Asp Tyr
225                 230                 235                 240
Tyr Pro Ser Asn Cys Glu Leu Asn Ala Ile Thr Ser Ala Ala Val Glu
                245                 250                 255
Ala Cys Asp Glu Ala Asp Gly Leu Lys Asp Asp Val Val Val Arg Thr
                260                 265                 270
Trp Glu Cys Glu Phe Asp Ala Ser Ser Val Val Gly Gln Lys Tyr Ser
            275                 280                 285
Cys Gly Asn Glu Ser Gly Ile Ile Thr Ser Gln Ala Ala Glu Val Ala
    290                 295                 300
Ser Thr Thr Trp Ser Gly Ser Val Phe Gln Asn Gly Arg Arg Ala Gly
305                 310                 315                 320
Trp Gly Leu Ala Pro Ser Ala Pro Leu Val Gly Ile Ala Asn Val Val
                325                 330                 335
Cys Ser Ser Pro Gly Asp Cys Glu Pro Ala Pro Phe Ile Leu Ser Thr
                340                 345                 350
Gln Trp Ile Ser Lys Phe Val Leu Glu Asn Ser Asp Ala Asp Leu Ser
            355                 360                 365
Thr Leu Thr Asp Glu Glu Tyr Leu Ser Leu Phe Arg Gln Ser Ala Asn
    370                 375                 380
Lys Tyr Ser Ser Leu Ser Asp Thr Asn Asp Pro Asp Leu Thr Asp Phe
385                 390                 395                 400
Lys Leu Ala Gly Gly Lys Met Ile Thr Trp His Gly Gly Asp Ile
                405                 410                 415
Leu Ile Pro Tyr Asn Ser Thr Val Asp Tyr Tyr Glu Lys Val Ala Ala
                420                 425                 430
Leu Asp Ala Asp Val Leu Asp Tyr Phe Arg Phe Ser Ala Pro Gly
            435                 440                 445
Val Gln His Cys Gln Asp Gly Ala Gly Trp Phe Pro Gly Glu Ala Phe
    450                 455                 460
Glu Ser Leu Val Asp Trp Val Glu Asn Gly Lys Ala Pro Glu Thr Leu
```

```
                465                 470                 475                 480
Tyr Gly Arg Pro Arg Gly Ser Asn Phe Thr Gly Glu Arg Glu Ala Asn
                        485                 490                 495
Leu Cys Leu Tyr Pro Lys Gln Ile Arg Tyr Ile Gly Gly Asp Pro Glu
            500                 505                 510
Val Ala Ser Ser Phe Glu Cys Gln
        515                 520

<210> SEQ ID NO 3
<211> LENGTH: 19
<212> TYPE: PRT
<213> ORGANISM: Myrothecium sp.

<400> SEQUENCE: 3

Ser Ser Cys Ser Pro Glu Val Phe Ser Ser Val Gly Ile Pro Lys Gly
1               5                   10                  15

Glu Val Leu

<210> SEQ ID NO 4
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: r is t or c
<220> FEATURE:
<221> NAME/KEY: misc_feature
<222> LOCATION: (12)..(12)
<223> OTHER INFORMATION: n is a, t, c or g
<220> FEATURE:
<221> NAME/KEY: misc_feature
<222> LOCATION: (15)..(15)
<223> OTHER INFORMATION: d is a or g
<220> FEATURE:
<221> NAME/KEY: misc_feature
<222> LOCATION: (18)..(18)
<223> OTHER INFORMATION: n is a, t, c or g

<400> SEQUENCE: 4
gtcggcatnc cnaanggnga                                         20

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
ccactccagg ttgtggaagc aac                                     23

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
cagccgttcc agtacgagta ttc                                     23

<210> SEQ ID NO 7
<211> LENGTH: 24
<212> TYPE: DNA
```

<213> ORGANISM: Artificial Sequence
<220> FEATURE:
<223> OTHER INFORMATION: primer

<400> SEQUENCE: 7
cgaagcgacc attccagtcc tcga                                          24

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
atgcaatcgc cgttagtaaa agtc                                          24

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
tctaggcttg cccattcgct ccta                                          24

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
tcctgtcgaa cagccgttcc agtacgagta ttcttg                             36

<210> SEQ ID NO 11
<211> LENGTH: 38
<212> TYPE: DNA
<213> ORGANISM: Artificial Sequence
<220> FEATURE:
<223> OTHER INFORMATION: primer

<400> SEQUENCE: 11
tactcgtact ggaacggctg ttcgacagga ggacgtca                           38

<210> SEQ ID NO 12
<211> LENGTH: 37
<212> TYPE: DNA
<213> ORGANISM: Artificial Sequence
<220> FEATURE:
<223> OTHER INFORMATION: primer

<400> SEQUENCE: 12
ggatgggtaa tagtccaatg atctcatggt cagaatg                            37

<210> SEQ ID NO 13
<211> LENGTH: 38
<212> TYPE: DNA
<213> ORGANISM: Artificial Sequence
<220> FEATURE:
<223> OTHER INFORMATION: primer

<400> SEQUENCE: 13
accatgagat cattggacta ttacccatcc aactgcga                           38

```
<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
caactgggga tccaccatgc aatcgccgtt ag                              32

<210> SEQ ID NO 15
<211> LENGTH: 38
<212> TYPE: DNA
<213> ORGANISM: Artificial Sequence
<220> FEATURE:
<223> OTHER INFORMATION: primer

<400> SEQUENCE: 15
caaaaccggc tcgagctcat gacactcgaa agaagaag                        38
```